United States Patent [19]

Anderson, Jr. et al.

[11] 4,151,001

[45] Apr. 24, 1979

[54] BEESWAX SUBSTITUTES

[75] Inventors: Gilbert L. Anderson, Jr., Wyncote, Pa.; Frederick P. Siegel, Lincolnwood, Ill.

[73] Assignee: Akzona Incorporated, Asheville, N.C.

[21] Appl. No.: 841,261

[22] Filed: Oct. 11, 1977

[51] Int. Cl.$^2$ .............................................. C08L 91/06
[52] U.S. Cl. ..................................... 106/270; 106/271; 560/199
[58] Field of Search ............... 106/268, 270, 271, 243; 260/410.9 R, 410.9 D; 560/199

[56] References Cited

U.S. PATENT DOCUMENTS

| | | | |
|---|---|---|---|
| 2,015,088 | 9/1935 | Reid ....................................... | 560/190 |
| 2,427,255 | 9/1947 | Burrell ................................... | 106/27 |
| 2,589,306 | 3/1952 | Steiner ................................... | 106/31 |
| 2,862,013 | 11/1958 | Miller et al. ..................... | 260/410.9 D |
| 2,911,309 | 11/1959 | Rudel et al. ......................... | 106/14.29 |
| 3,073,706 | 1/1963 | Treboux ................................. | 106/10 |
| 3,088,928 | 5/1963 | Berres et al. ........................... | 560/199 |
| 3,127,440 | 3/1964 | Sims ...................................... | 106/271 |
| 3,914,131 | 10/1975 | Hutchinson ........................... | 106/271 |

Primary Examiner—Theodore Morris
Attorney, Agent, or Firm—Francis W. Young; Robert F. Green

[57] ABSTRACT

Compositions useful as substitutes for natural beeswax are disclosed. Such compositions comprise a reaction product obtained by reacting under esterification conditions (1) an alcohol containing from about 10 to about 22 carbon atoms, (2) a glycolic component selected from the group consisting of ethylene glycol, propylene glycol, polyoxyethylene glycol having a molecular weight from about 100 to about 1500, and polyoxypropylene glycol having a molecular weight from 150 to about 1025, and (3) a difunctional acid containing from about 7 to about 36 carbon atoms. The foregoing reaction product may be optionally mixed with other esters, or with minor amounts of natural beeswax.

17 Claims, No Drawings

BEESWAX SUBSTITUTES

BACKGROUND OF THE INVENTION

This invention relates to substitutes for natural beeswax.

Natural beeswax has been utilized in various cosmetic formulations for nearly 2,000 years. Yet, to date, very few effective substitutes for natural beeswax have been found. Beeswax, of course, is a secretion of the worker bee, which contains various hydrocarbons, fatty alcohols, fatty acids, and esters, the compostion of which will vary from source to souce. The exact compostion is highly complex, and essentially impossible to duplicate exactly. Listed in Table I is a generally accepted composition for yellow beeswax.

TABLE I

| YELLOW BEESWAX | |
|---|---|
| Esters of wax acids: | 71% |
| Simple esters: | |
| Myricyl palmitate, $C_{15}H_{31}CO.O.C_{30}H_{61}$ (23%) | |
| Lacceryl palmitate, $C_{15}H_{31}CO.O.C_{32}H_{65}$ (2%) | |
| Myricyl cerotate, $C_{26}H_{53}CO.O.C_{30}H_{61}$ (12%) | |
| Myricyl hypogaeate, $C_{15}H_{29}CO.O.C_{30}H_{61}$ (12%) | |
| Hydroxy esters: | |
| Ceryl hydroxypalmitate, | |
| $C_{15}H_{30}(OH).CO.O.C_{26}H_{53}$ (8–9%) | |
| Acid esters (4–4.5%) | |
| Diesters (6–6.5%) | |
| Acid diesters, triesters, hydroxy diesters (3–3.5%) | |
| Cholesteryl esters of fatty acids: | 1% |
| Cholesteryl isovalerate | |
| Coloring matter: 1,3-hydroxyflavone (mp 285° C.) | 0.3% |
| Lactone: ω-myristolactone (mp 33°–34° C.) | 0.6% |
| Free alcohols: $C_{34}$–$C_{36}$ | 1–1.25% |
| Free wax acids | 13.5–14.5% |
| Normal acids (mp 77.5°–70° C., molecular weight 412) | |
| Saturated: | |
| Lignoceric acid (1–1.5%) | |
| Cerotic acid (3.8–4.4%) | |
| Montanic acid | |
| Melissic acid (2%) | |
| Psyllic acid (1.3–1.5%) | |
| Unsaturated: | |
| Hypogaeic acid, $C_{16}H_{30}O_2$ (1.5%) | |
| Hydrocarbons: | 10.5–13.5% |
| Saturated: | |
| Pentacosane, $C_{25}H_{52}$ (0.3%) | |
| Heptacosane, $C_{27}H_{56}$ (0.3%) | |
| Nonacosane, $C_{29}H_{60}$ (1–2%) | |
| Hentriacontane, $C_{31}H_{64}$ (8–9%) | |
| Unsaturated: | |
| Melene, $C_{30}H_{60}$ (2.5%) | |
| Moisture and mineral impurities | 1–2% |
| Mean molecular weight | 570 |
| Ester number | 72–76 |

In recent years there has been a great endeavor to develop commercially acceptable synthetic beeswax compositions. The reasons for such an endeavor are basically two-fold, (1) the need to supplement the supply of natural beeswax and (2) the need of cosmetic formulators to obtain compositions having consistent physical properties so that it is not necessary to reformulate every time a new lot of natural beeswax is utilized in production.

U.S. Pat. Nos. 3,754,033; 3,914,131; and B 303,702, represent one manufacturer's endeavor to obtain a satisfactory synthetic beeswax composition.

The foregoing U.S. patents all deal with a synthetic beeswax substitute. Such a substitute comprises (1) a high molecular weight α-alkyl substituted branched monocarboxylic acid containing from about 20 to about 60 carbon atoms, the alkyl branching containing from about 1 to about 16 carbon atoms, (2) a microcrystalline petroleum wax, and (3) mixed glycerides of saturated mono- and di-carboxylic acids selected from the group consisting of Japan wax and compositions obtained by the reaction of 1 to 4 moles of a monocarboxylic acid containing 14 to 20 carbon atoms, 0.25 to 1.5 moles of a short-chained dicarboxylic acid containing 6 to 12 carbon atoms and 1 mole of glycerine.

The foregoing U.S. patents also indicate that other synthetic substitutes for natural beeswax have been suggested, such as the esterification product for montanic acid, ethylene glycol, and oxidized paraffin, as well as the waxes obtained by esterifying pentaerythritol with saturated fatty acids and maleic anhydride. It has also been indicated that other substitutes for natural beeswax are the products obtained by oxidizing high melting ozocerites and ceresins which are subsequently esterified with an alcohol containing from 1 to 30 carbon atoms.

U.S. Pat. No. 3,073,706 teaches that certain esters of mono- and poly-carboxylic acids containing at least 10 carbon atoms and mono- and poly-hydric alcohols containing at least 2 carbon atoms may be utilized in the waxy portion of aerosol floor care preparations. U.S. Pat. No. 3,127,440 discloses that the dialkyl ($C_{30}$ to $C_{60}$) esters of 1,4-dicarboxylic acids 4 carbon atoms are useful as hard wax formulations. U.S. Pat. No. 2,911,309 discloses that certain ester products are useful as rust preventive compostions, there being no disclosure that such esters are useful as waxes of any sort.

Although, there have been available certain commercial synthetic beeswax formulations, there still exists a need for a commercially acceptable replacement for natural beeswax, especially for use in cosmetic formulations.

SUMMARY OF THE INVENTION

A replacement for beeswax has now been discovered which comprises the polyester reaction product obtained by reacting, under esterification conditions, (1) a difunctional aliphatic acid having from about 7 to about 36 carbon atoms, (2) an aliphatic alcohol having from about 10 to about 22 carbon atoms, and (3) a glycolic compound selected from the group consisting of ethylene glycol, propylene glycol, polyoxyethylene glycol having a molecular weight from about 100 to about 1500, and polyoxypropylene glycol having a molecular weight from about 150 to about 1025, the reactants being present in an amount such that the number of acid functionalities is approximately equal to the number of hydroxyl functionalities, the alcohol and the glycolic compounds each supplying at least 10% of the hydroxyl functionalities present, and the reaction being continued until an acid value from about 10 to about 30 is obtained.

A more preferred synthetic beeswax substitute is obtained by combining the foregoing polyester reaction product with a second constituent. One such second constituent is the reaction product obtained by reacting under esterification conditions about 2 moles of an aliphatic alcohol having from about 10 to about 30 carbon atoms with 1 mole of a difunctional aliphatic acid having from about 7 to about 36 carbon atoms, until an acid value of about 0 to about 30 is obtained. When such a composition is blended with the polyester reaction product identified above, the acid value exhibited by the blend should be between about 5 and about 30, preferably between about 10 and about 30. Thus, it is possible to utilize a polyester reaction product, as identified above, which has an acid value less than 5, so long as the blended components have an acid value between about 5 and about 30, preferably between about 10 and about 30.

An alternative blend comprises the polyester reaction product identified above, with a reaction product obtained by reacting under esterification conditions an aliphatic acid having from about 12 to about 30 carbon atoms with a branched chain alcohol having from about 32 to about 36 carbon atoms, to obtain an acid value from about 0 to about 30. Again, the only critical factor with respect to the acid value is that the blended system containing the two reaction products exhibit an acid value between about 5 and about 30, preferably between about 10 and about 30.

It has also been discovered that especially desirable compositions are obtained if from about 10 to about 20 percent of the synthetic substitute, whether a polyester alone or blended with a second ester component, is replaced with an equal weight amount of natural beeswax.

DESCRIPTION OF THE PREFERRED EMBODIMENTS

As indicated, the primary substitute for beeswax provided by this invention is a polyester reaction product obtained from a difunctional acid, an alcohol, and a glycolic compound. The difunctional acids useful in the practice of the present invention are any aliphatic difunctional acids having from about 7 to about 36 carbon atoms. Preferably, the difunctional acid will contain from about 10 to about 18 carbon atoms, those difunctional acids containing about 12 carbon atoms being most preferable. Thus, a particularly advantageous difunctional acid useful in the practice of the present invention is dodecanedioic acid.

The alcohols useful in forming the three-component polyester reaction product are those aliphatic alcohols which contain from about 10 to about 22 carbon atoms. Exemplary of the alcohols useful in the practice of the present invention are dodecyl alcohol, tetradecyl alcohol, hexadecyl alcohol, and octadecyl alcohol.

The glycolic compounds useful in the present invention include ethylene glycol and propylene glycol. Also useful are those polyoxyethylene glycols having a molecular weight from about 100 to about 1500, preferably those polyoxyethylene glycols having a molecular weight from about 100 to about 1000. The polyoxypropylene glycols having a molecular weight from about 150 to about 1025, preferably those having a molecular weight from about 150 to about 425, are likewise useful.

The three components are reacted in a molar ratio such that the number of acid functionalities is approximately equal to the number of hydroxyl functionalities. It is also desirable that the alcohol and the glycolic compounds each supply at least 10% of the hydroxyl functionalities which are present in the reaction. It is usually preferable for the components to be reacted so that about 2 moles of the difunctional acid are reacted with about 2 moles of the alcohol and about 1 mole of the glycolic compound.

As naturally occurring beeswax contains free fatty acids, it is preferable for the polyester to also contain a quantity of free fatty acids. Thus, the final reaction product should have an acid value between about 10 and about 30. However, if the polyester reaction product is to be subsequently blended with another component to make the desired synthetic beeswax formulation, the acid values may vary outside of the foregoing range, so long as the blended material has an acid value between about 5 and about 30, preferably between about 10 and about 30.

The polyester reaction product is made by reacting the aforementioned three components under typical esterification conditions. The exact reaction conditions for performing the esterification are not critical, and any acceptable esterification conditions may be utilized. In a typical esterification reaction, the three components may be charged to a reaction vessel and heated until molten. Nitrogen may then be sparged through the reaction mixture which is subsequently heated to about 240° C., while maintaining the vapor temperature below 105° C. The reaction mixture may then be held at such a temperature for an extended period of time, such as twelve hours, or until an acid value of less than about 30 is obtained. The foregoing process parameters are exemplary only, and, as stated, are not critical to the present invention.

The polyester reaction product is, by itself, a good substitute for natural beeswax. However, to improve the physical properties of the material, it is preferable to blend the polyester material with a second component. One possible second component which is especially useful in forming a synthetic beeswax formulation is the reaction product obtained by reacting under esterification conditions about 2 moles of an aliphatic alcohol containing from about 10 to about 30 carbon atoms with about 1 mole of a difunctional acid containing from about 7 to about 36 carbon atoms, until an acid value of about 0 to about 30 is obtained. The acid value is not critical, and as previously stated, it is only preferable that the reaction product's acid value fall within this range. The primary criteria with respect to the acid value is that the reaction product, when blended with the polyester reaction product, form a mixture which exhibits an acid value from about 5 to about 30, preferably from about 10 to about 30.

The alcohols useful in producing such an ester are aliphatic alcohols having from about 10 to about 30 carbon atoms, those aliphatic alcohols having from about 10 to about 18 carbon atoms being preferred, and especially preferred are those aliphatic alcohols having from about 12 to about 18 carbon atoms.

The difunctional acids useful in making such an ester are those having from about 7 to about 36 carbon atoms, those difunctional acids having from about 10 to about 18 carbon atoms being especially preferred and most preferred is dodecanedioic acid.

Another possible second component which may be blended with the polyester material is the reaction product obtained by reacting under esterification conditions an aliphatic acid having from about 12 to about 30 carbon atoms with a branched chained alcohol having from about 32 to about 36 carbon atoms. The aliphatic acid preferably contains from about 12 to about 18 carbon atoms, and most preferably is tetradecanoic acid. The acid and alcohol are reacted in a molar ratio of about 1:1, and the reaction is carried out until an acid value of about 0 to about 30 is obtained.

The polyester reaction product may be blended with either the difunctional acid ester or the monofunctional acid ester, as described above, in a weight ratio of polyester to ester of about 2:1 to about 1:2. Preferably, the polyester and the ester reaction products are blended in a weight ratio of about 1:1.

The present invention will be described in more detail in the following Examples which are meant to be exemplary only and are not limitations upon the scope of the present invention.

EXAMPLE I

A polyester reaction product is made by adding 556 grams (2 moles) of commercial octadecyl alcohol, 62 grams (1 mole) of ethylene glycol, and 460 grams (2 moles) of commercial dodecanedioic acid to a reactor and heating the mixture until molten. Nitrogen is then sparged through the reaction mixture which is subsequently heated slowly to a temperature of about 240° C., while maintaining the vapor temperature below about 105° C. The reaction mixture is maintained at about 240° C. for about twelve hours, until the acid value is less than about 30. The final product is an effective beeswax substitute having an acid value of 24.8, a saponification value of 227 and a melting point of 70.9° C.

EXAMPLE II

A second reaction product is made by charging 230 grams (1 mole) of commercial dodecanedioic acid and 539.0 (2 moles plus 10% excess) of commercial hexadecyl alcohol to a reactor and then heating the reaction mixture to a temperature of about 240° C. under a nitrogen sparge. The reactants are maintained at about 240° C. for approximately twelve hours, or until the acid value is less than about 3. The reaction mixture is cooled to about 150° C., the nitrogen sparge terminated, and a vacuum (4 mm. Hg or less) applied. The reaction mixture is then heated to about 250° C., under a vacuum to remove excess alcohol, and the reaction mixture is maintained at a temperature of about 250° C. for approximately fifteen minutes. Subsequently, the reaction mixture is cooled to about 150° C. and the vacuum carefully removed. The resulting product has an acid value of 2.75, a saponification value of 161 and a melting point of 64.1° C.

EXAMPLE III

The reaction products of Example I and Example II are blended at a weight ratio of 1:1 to yield a synthetic product having the same general physical properties as natural beeswax.

EXAMPLE IV

The process of Example II is followed utilizing as the reactants tetradecanoic acid and a mixture of branched-chain aliphatic alcohols having from about 30 to about 36 carbon atoms, supplied by Henkel under the designation Standamul GT 32-36, in a 1:1 molar ratio. The alcohol has a straight-chain carbon backbone and an essentially centrally located methylol group, the mixture containing approximately 33 percent $C_{32}$, 33 percent $C_{37}$, 15 percent $C_{36}$ alcohols and the balance having chain lengths above $C_{36}$ and below $C_{32}$. The resulting product has an acid value of 4.0, a saponification value of 87 and a melting point of 29.4° C.

EXAMPLE V

The process of Example II is followed utilizing as the reactants dodecanedioic acid and dodecyl alcohol. The resulting product has an acid value of 2.4, a saponification value of 198 and a melting point of 51.4° C.

EXAMPLE VI

The process of Example II is followed utilizing as the reactants dodecanedioic acid and octadecyl alcohol. The resulting product has an acid value of 2.9, a saponification value of 148 and a melting point of 58.8° C.

EXAMPLE VII

The process of Example I is followed utilizing as the reactants 1 mole of propylene glycol, 2 moles of dodecanedioic acid, and 2 moles of octadecyl alcohol. The resulting product has an acid value of 26, a saponification value of 213 and a melting point of 63.5° C.

EXAMPLE VIII

The process of Example I is followed utilizing as the reactants 1 mole of polyoxyethylene glycol (200), 2 moles of dodecanedioic acid, and 2 moles of octadecyl alcohol. The resulting product has an acid value of 12, a saponification value of 197 and a melting point of 64.4° C.

EXAMPLE IX

The process of Example I is followed utilizing as the reactants 1 mole of ethylene glycol, 2 moles of dodecanedioic acid, and 2 moles of dodecyl alcohol. The resulting product has an acid value of 22, a saponification value of 270 and a melting point of 67.5° C.

EXAMPLE X

The process of Example I is followed utilizing as the reactants 1 mole of polyoxyethylene glycol (1000), 2 moles of dodecanedioic acid, and 2 moles of octadecyl alcohol. The resulting product has an acid value of 7.8, a saponification value of 115 and a melting point of 67.2° C.

To demonstrate the efficacy of the compositions of the present invention as replacements for natural beeswax, various combinations of the products of the foregoing Examples were combined and utilized as replacements for beeswax in the standard USP cold cream formula which is 56% mineral oil, 18% beeswax, 25.5% deionized water, and 0.5% sodium borate. The formula is manufactured by combining all oil phase ingredients, the mineral oil and beeswax, heating the mixture until melting occurs, adding the sodium borate to the water, heating the same to 70° C., and finally adding the borax solution to the oil phase with mixing. The resulting composition is cooled to approximately 45°–50° C. and poured into jars.

For purposes of evaluating the composition of the present invention, the natural beeswax in the USP cold cream formula was replaced with 9% of a three-component polyester, in accordance with the present invention, and 9% of an ester reaction product, also in accordance with the present invention. The resulting compositions were then compared to the standard USP formula containing beeswax, with respect to the opacity, stability, gloss, and texture of the resultant materials. In particular, it is desirable for the formulations to show a degree of whiteness, that is, a lack of translucency. Also, the formulations should be stable for at least 45 days at 45° C. and the surface of the cream should demonstrate a gloss, as it does with natural beeswax. Also, the texture of the material should demonstrate a smoothness, that is, a lack of graininess, and should also be as firm as the composition containing natural beeswax. It should be understood that all of the foregoing physical characteristics are not necessary for a commercially viable synthetic beeswax. Examples XI-XVII are blends of various components formed by Examples I-X having the compositions indicated in Table II. The compositions were analyzed for their physical properties and the comments relating thereto are also contained in Table II.

TABLE II

Cold Cream Formulas Containing Synthetic Beeswax

| Example No. | Ester Product of Example No. | Polyester Product of Example No. | |
|---|---|---|---|
| XI | V | I | Stable, very soft cream, no gloss |
| XII | II | I | Excellent texture and stability, best gloss |
| XIII | VI | I | Stable, soft, no gloss |
| XIV | II | VII | Stable, firmest cream-firmer than natural beeswax, gloss similar to Example XII |
| XV | II | VIII | Very good texture and whiteness, no gloss |
| XVI | II | IX | Viscosity between Examples XIV and XV, no gloss, opacity poor good stability |
| XVII | II | X | No gloss, whiter than Example XVI, less white than Example XV, viscosity similar to Example XVI, good stability |

The products of Examples XI-XVII were judged to be suitable replacements for synthetic beeswax. However, certain of the compositions suffered from various physical properties which were not as desirable as those of natural beeswax, especially with respect to gloss. It has been determined that the gloss of the foregoing compositions may be improved by incorporating a minor amount of natural beeswax into the formulations. Thus, a formulation similar to that of Example XII has been made, replacing from about 10% to about 20% of the products of Examples I and II with natural beeswax. The resulting cold cream formulation resulted in a product which was virtually indistinguishable from the cold cream containing all natural beeswax.

What is claimed is:

1. A composition useful as a substitute for natural beeswax comprising, a reaction product obtained by reacting, under esterification conditions,
   (a) a difunctional aliphatic acid having from about 7 to about 36 carbon atoms;
   (b) an aliphatic alcohol having from about 10 to about 22 carbon atoms; and
   (c) a glycolic compound selected from the group consisting of ethylene glycol, propylene glycol, polyoxyethylene glycol having a molecular weight from about 100 to about 1500, and polyoxypropylene glycol having a molecular weight from about 150 to about 1025;
the reactants being present in an amount such that the number of acid functionalities is approximately equal to the number of hydroxyl functionalities; the alcohol and glycolic compounds each supplying at least 10 percent of the hydroxyl functionalities present; and the reaction being continued until the reaction mixture has attained an acid value from about 10 to about 30.

2. The composition of claim 1, wherein the acid contains from about 10 to about 18 carbon atoms.

3. The composition of claim 1, wherein the acid is dodecanedioic acid.

4. The composition of claim 1, wherein the glycolic compound is ethylene glycol.

5. The composition of claim 1, wherein the glycolic compound is propylene glycol.

6. The composition of claim 1, wherein the glycolic compound is polyoxyethylene glycol having a molecular weight from about 100 to about 1500.

7. The composition of claim 6, wherein the polyoxyethylene glycol has a molecular weight from about 100 to about 1000.

8. The composition of claim 1, wherein the glycolic compound is polyoxypropylene glycol having a molecular weight from about 150 to about 1025.

9. The composition of claim 8, wherein the polyoxypropylene glycol has a molecular weight from about 150 to about 425.

10. The composition of claim 1, wherein the alcohol is selected from the group consisting of dodecyl alcohol, tetradecyl alcohol, hexadecyl alcohol, and octadecyl alcohol.

11. The composition of claim 1, further comprising from about 10 to about 20 percent of natural beeswax, based on the total weight of the composition.

12. A composition useful as a substitute for natural beeswax comprising (A) a reaction product obtained by reacting, under esterification conditions,
   (a) a first difunctional aliphatic acid having from about 7 to about 36 carbon atoms;
   (b) a first aliphatic alcohol having from about 10 to about 22 carbon atoms; and
   (c) a glycolic compound selected from the group consisting of ethylene glycol, propylene glycol, polyoxyethylene glycol having a molecular weight from about 100 to about 1500, and polyoxypropylene glycol having a molecular weight from about 150 to about 1025;
the reactants being present in an amount such that the number of acid functionalities is approximately equal to the number of hydroxyl functionalities; the alcohol and glycolic compounds each supplying at least 10 percent of the hydroxyl functionalities present; and the reaction being continued until the reaction mixture has attained an acid value from about 0 to about 30; and (B) a reaction product obtained by reacting under esterification conditions;
   (a) about 2 moles of a second aliphatic alcohol having from about 10 to about 30 carbon atoms; and
   (b) about 1 mole of a second difunctional aliphatic acid having from about 7 to about 36 carbon atoms;
the reaction being carried out until the reaction mixture has obtained an acid value of from about 0 to about 30; components A and B being mixed in a weight ratio of from about 1:2 to about 2:1 and the mixture having an acid value of from about 5 to about 30.

13. The composition of claim 12, wherein the first difunctional acid contains from about 10 to about 18 carbon atoms, the second aliphatic alcohol contains from about 12 to about 18 carbon atoms and the second difunctional acid contains from about 10 to about 18 atoms.

14. The composition of claim 12, further comprising from about 10 to about 20 percent of natural beeswax, based on the total weight of the composition.

15. A composition useful as a substitute for natural beeswax comprising (A) a reaction product obtained by reacting, under esterification conditions, (a) a difunctional aliphatic acid having from about 7 to about 36 carbon atoms;
(b) an aliphatic alcohol having from about 10 to about 20 carbon atoms; and
(c) a glycolic compound selected from the group consisting of ethylene glycol, propylene glycol, polyoxyethylene glycol having a molecular weight from about 100 to about 1500, and polyoxypropylene glycol having a molecular weight from about 150 to about 1025;

the reactants being present in an amount such that the number of acid functionalities is approximately equal to the number of hydroxyl functionalities; the alcohol and glycolic compounds each supplying at least 10 percent of the hydroxyl functionalities present; and the reaction being continued until the reaction mixture has attained an acid value from about 0 to about 30; and (B) a reaction product obtained by reacting under esterification conditions;

(a) an aliphatic acid having from about 12 to about 30 carbon atoms; and
(b) a branched-chain alcohol having from about 32 to about 36 carbon atoms;

the reaction being carried out until the reaction mixture has obtained an acid value of from about 0 to about 30; components A and B being mixed in a weight ratio of from about 1:2 to about 2:1 and the mixture having an acid value from about 10 to about 30.

16. The composition of claim 15, wherein the difunctional acid contains from about 10 to about 18 carbon atoms and the monofunctional acid contains from about 12 to about 18 carbon atoms.

17. The composition of claim 15, further comprising from about 10 to about 20 percent of natural beeswax, based on the total weight of the composition.

* * * * *